(12) United States Patent
Karasawa et al.

(10) Patent No.: US 7,306,599 B2
(45) Date of Patent: Dec. 11, 2007

(54) MEDICAL INSTRUMENT AND MEDICAL INSTRUMENT SYSTEM

(75) Inventors: Hitoshi Karasawa, Tokyo (JP); Tetsumaru Kubota, Tokyo (JP)

(73) Assignee: Olympus Corporation (JP)

( * ) Notice: Subject to any disclaimer, the term of this patent is extended or adjusted under 35 U.S.C. 154(b) by 114 days.

(21) Appl. No.: 10/896,428

(22) Filed: Jul. 22, 2004

(65) Prior Publication Data

US 2005/0021017 A1    Jan. 27, 2005

(30) Foreign Application Priority Data

Jul. 24, 2003    (JP) .............................. 2003-201065

(51) Int. Cl.
*A61B 18/18*    (2006.01)

(52) U.S. Cl. ........................................... 606/51; 606/50

(58) Field of Classification Search ............ 606/41–52, 606/27–31
See application file for complete search history.

(56) References Cited

U.S. PATENT DOCUMENTS 5,540,684 A * 7/1996 Hassler, Jr. ................. 606/40
5,716,366 A * 2/1998 Yates .......................... 606/139
5,792,137 A * 8/1998 Carr et al. ..................... 606/29
6,626,901 B1    9/2003 Treat et al. ................... 606/29
6,773,434 B2 * 8/2004 Ciarrocca ..................... 606/51
6,821,273 B2 * 11/2004 Mollenauer .................. 606/28
2003/0073987 A1 * 4/2003 Sakurai et al. ............... 606/28
2003/0171747 A1 * 9/2003 Kanehira et al. ............. 606/45

FOREIGN PATENT DOCUMENTS

| JP | 8-294494 | 11/1996 |
|---|---|---|
| JP | 2001-198137 | 7/2001 |
| JP | 2001-340349 | 12/2001 |

* cited by examiner

*Primary Examiner*—Michael Peffley
(74) *Attorney, Agent, or Firm*—Ostrolenk, Faber, Gerb & Soffen, LLP (57) ABSTRACT

A medical instrument includes an elongated insertion section, a pair of holding portions which hold tissue, a heat source portion, and an operation section which relatively opens/closes the holding portions. The holding portions are provided at a distal end portion of the insertion section. The heat source portion is provided to at least one of the holding portions, generates heat, and transfers the heat toward the other holding portion. At least a part of the heat source portion is covered with an insulating member provided to the holding portions. The operation section is provided at a proximal end portion of the insertion section.

18 Claims, 9 Drawing Sheets

MEDICAL INSTRUMENT AND MEDICAL INSTRUMENT SYSTEM

CROSS-REFERENCE TO RELATED APPLICATIONS

This application is based upon and claims the benefit of priority from prior Japanese Patent Application No. 2003-201065, filed Jul. 24, 2003, the entire contents of which are incorporated herein by reference.

BACKGROUND OF THE INVENTION

1. Field of the Invention

The present invention relates to a medical instrument and a medical instrument system which perform a surgical procedure such as coagulation/hemostasis or incision with respect to tissue.

2. Description of the Related Art

In order to perform a surgical procedure such as coagulation/hemostasis or incision with respect to tissue, there is generally known a medical instrument including a pair of jaws which are opened/closed and hold tissue, and an operation section used to open/close these jaws. A heater element which generates heat when energized is provided to one or both of the jaws in the medical instrument. Generating the heat by the heater element when tissue is held between the jaws of such a medical instrument enables a heat treatment for, e.g., coagulation of the tissue or incision of coagulated tissue. Therefore, the medical instrument is usually utilized in various surgical cases such as stanching of blood included in tissue, cautery or coagulation of a diseased part or a bleeding part in a surface layer of tissue, or occlusion of an oviduct for the purpose of contraception.

When conducting various surgical procedures such as blood stanching, cautery, coagulation, occlusion or incision of tissue by using the medical instrument, compression, grasping, exfoliation or the like of target tissue or peripheral tissue is mechanically carried out by using surgical instruments such as an exfoliation forceps in advance before such surgical procedures. A surgical operation to assure a working (insertion) area of an endoscope, a visual field of an operator or a working area of a medical instrument is performed in advance.

For example, Jpn. Pat. Appln. KOKAI Publication No. 2001-198137 discloses a medical instrument in which a heater element such as a ceramic heater is provided to at least one of a pair of jaws which are opened/closed. In the medical instrument, a heater plate (treatment portion) which comes into contact with tissue and protrudes with an edged tool shape is provided to at least one jaw. A heater element as a heat source portion is fixed to the heater plate in order to transfer the heat generated by the heater element to the heater plate. Therefore, tissue which is in contact with or pressed against the heater plate can be subjected to a heat treatment.

Jpn. Pat. Appln. KOKAI Publication No. 2001-340349 discloses a medical instrument having a heater element such as a ceramic heater being provided to one of a pair of jaws. A heat-insulating member which comes into contact with the heater element is arranged to the other jaw. Therefore, when one jaw is in contact with the other jaw, heat is not released from the heater element, thereby improving the heat transfer efficiency of a treatment.

For example, Jpn. Pat. Appln. KOKAI Publication No. 8-294494 discloses a tweezers type high-frequency galvano-surgery medical instrument. The medical instrument electrically insulates respective parts other than electrode portions at ends of a tweezers type arms having the elasticity. A bipolar high-frequency current is passed between a pair of opposed electrodes of the arms with tissue sandwiched therebetween. Then, the tissue can be electrically coagulated or incised.

BRIEF SUMMARY OF THE INVENTION

According to an aspect of the present invention, a medical instrument includes:

an elongated insertion section having distal and proximal end portions;

a pair of holding portions which are provided at the distal end portion of the insertion section and hold tissue;

a heat source portion which is provided to at least one of the holding portions, generates heat to transfer the heat toward the other holding portion, at least a part of the heat source portion being covered with a insulating member provided to the holding portions; and an operation section which is provided at the proximal end portion of the insertion section, and opens/closes the holding portions.

Advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments according to the present invention will now be described hereinafter with reference to the accompanying drawings. A first embodiment will be explained by using FIGS. 1 to 6.

Figure 1:
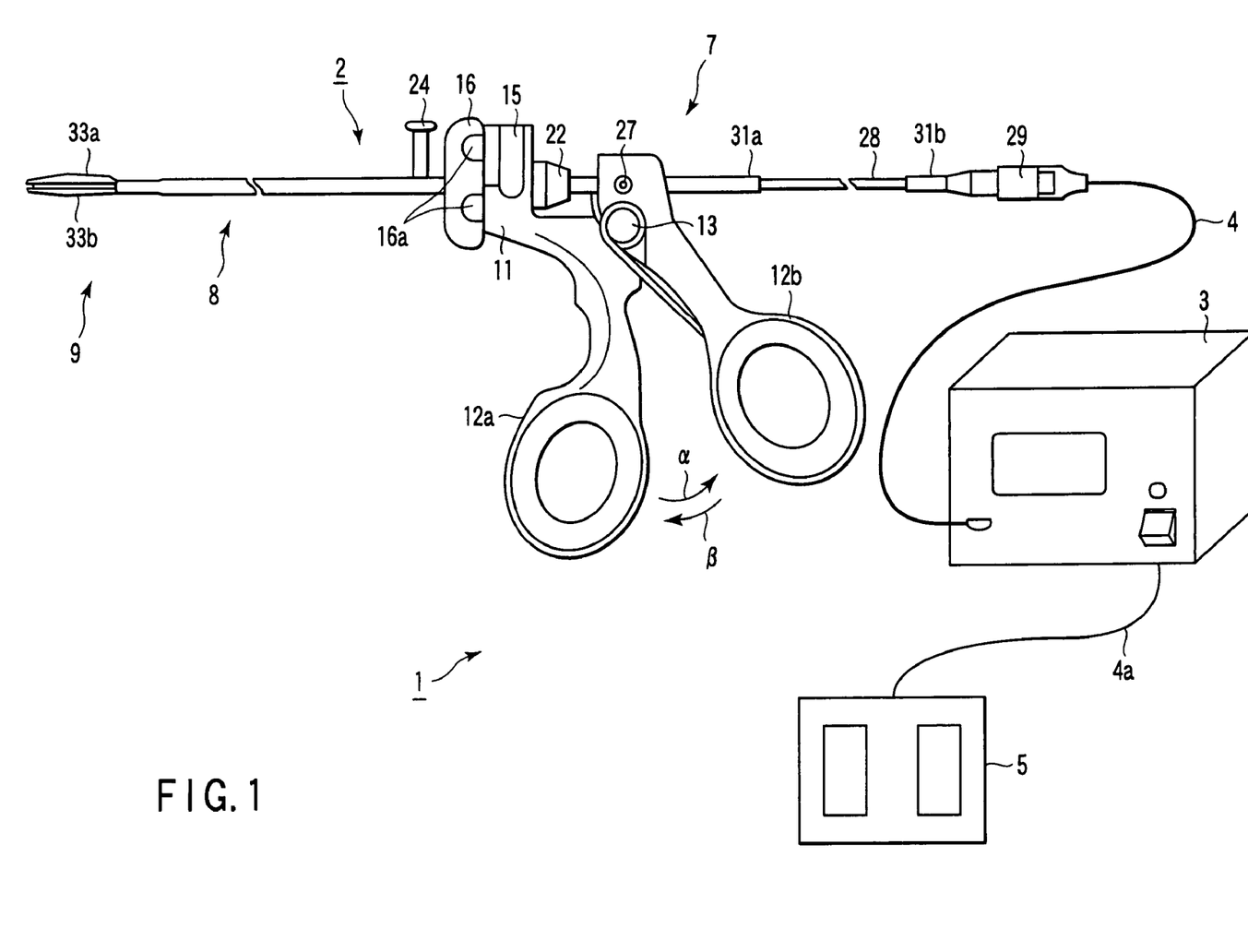
FIG. 1 is a schematic view showing a structure of a medical instrument system including a treatment instrument according to a first embodiment.

As shown in FIG. 1, a medical instrument system 1 according to the present embodiment includes a treatment instrument (thermo-coagulation and cutting forceps) 2 and a power supply apparatus 3. The instrument (medical instrument) 2 is electrically connected with the power supply apparatus 3 through a long connection cord 4. A foot switch 5 which is used to control ON/OFF of the power supply apparatus 3 or power (output) adjustment by a foot of an operator is connected with the power supply apparatus 3 through a connection cord 4a.

The instrument 2 includes an operation section 7 on a proximal side, an insertion section 8 whose proximal end portion is coupled with a distal end of the operation section 7, and a treatment portion (holding portions) 9 provided at a distal end of the insertion section 8. The operation section 7 includes an operation section main body 11. A fixed handle 12a is integrally provided to the operation section main body 11. The fixed handle 12a includes a pivot 13, and a movable handle 12b is pivoted on the pivot 13 to be capable of swiveling (opening/closing). That is, the movable handle 12b is supported to the fixed handle 12a by the pivot 13.

In the operation section main body 11, an insertion section fixing member 15 which supports the insertion section 8 is provided at an upper end portion of the fixed handle 12a. A rotational operation section (disk) 16 which swivels the insertion section 8 around its axis is provided on a distal end side of the insertion section fixing member 15. A slip stopper 16a obtained by aligning a plurality of concave portions along preferably a circumferential direction is formed at a rim portion of the rotational operation section 16.

Figure 2:
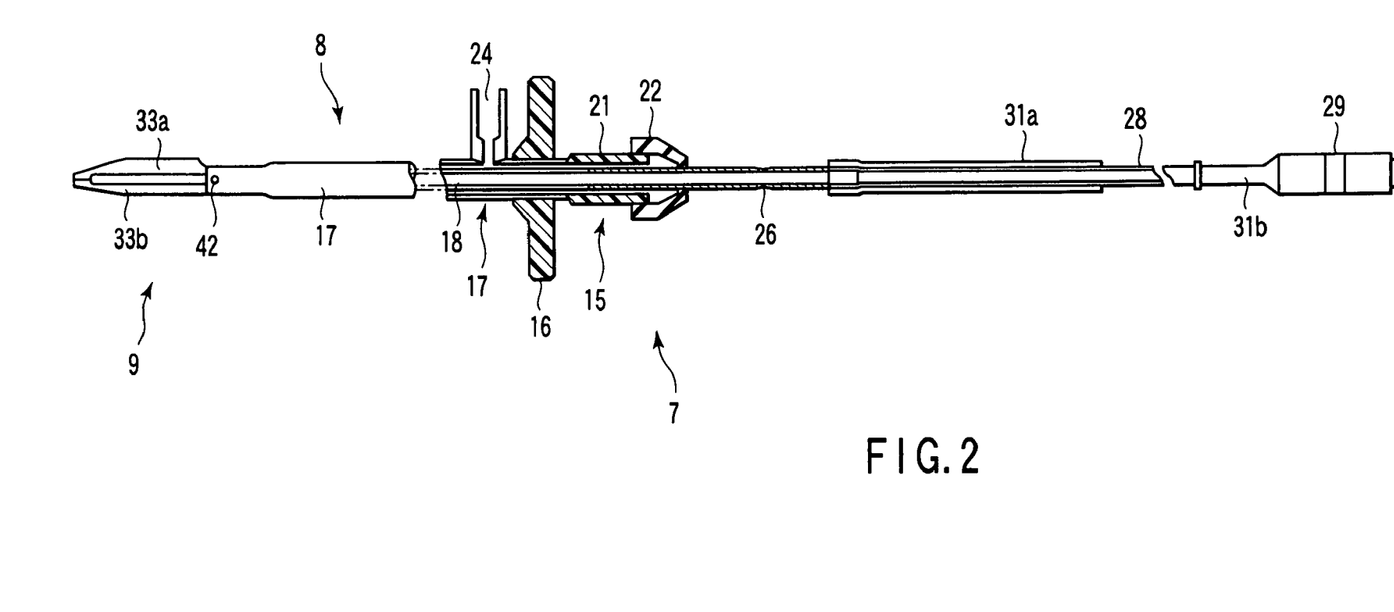
FIG. 2 is a schematic partial cross-sectional view showing the instrument in the medical instrument system according to the first embodiment.
Figure 3A:
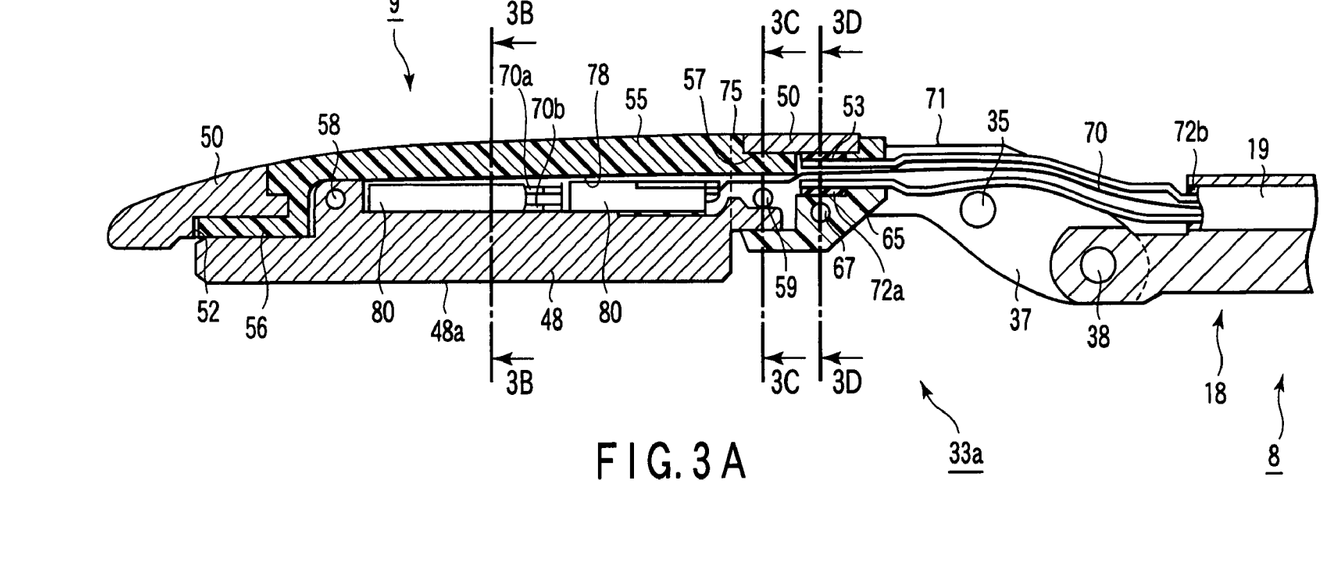
FIG. 3A is a schematic cross-sectional view showing a first jaw of the instrument in the medical instrument system according to the first embodiment.

As shown in FIG. 2, the insertion section 8 includes a pipe-like member 17 having a minor diameter, and a drive shaft (drive pipe) 18 which is inserted into the pipe-like member 17 and passed through to be capable of moving back and forth. As shown in FIG. 3A, a hole portion 19 is formed to the drive shaft 18 along an axial direction of the drive shaft 18. The hole portion 19 is passed through from the distal end portion to the proximal end portion of the drive shaft 18. That is, the drive shaft 18 is formed into a pipe shape.

Figure 4:
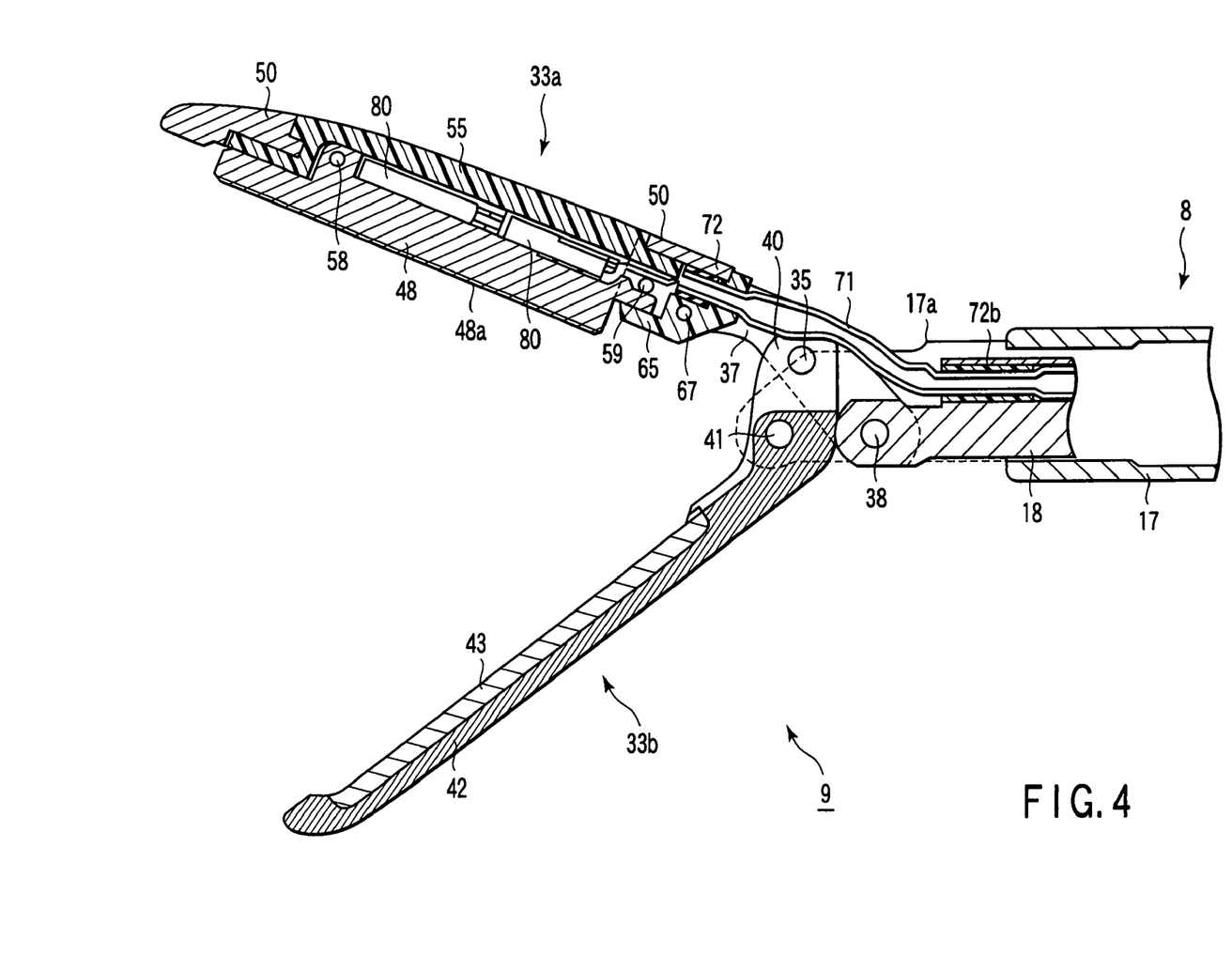
FIG. 4 is a schematic cross-sectional view showing a treatment portion of the instrument in the medical instrument system according to the first embodiment.

As shown in FIG. 4, a protrusion 17a which protrudes toward the front side and is connected with a later-described second jaw 33b is integrally formed at the distal end portion of the pipe-like member 17. As shown in FIG. 2, the front side of the pipe-like member 17 is armored with a cylindrical insertion section main body 21. The insertion section main body 21 is detachably attached to the insertion section fixing member 15 of the operation section 7 in such a manner that it can freely swivel. A seal member 22 which seals an outer periphery of the drive shaft 18 is provided at a rear end portion of the insertion section main body 21. The drive shaft 18 pierces the seal member 22 and extends toward the rear side. Therefore, even if the drive shaft 18 moves forward or rearward with respect to the insertion section main body 21 in the axial direction, a portion between the insertion section main body 21 and the drive shaft 18 is water-tightly or air-tightly maintained by the seal member 22.

The above-described discoid rotational operation section 16 is arranged on the distal end side of the insertion section main body 21. On the distal end side of the rotational operation section 16 is provided, e.g., a cleansing port 24 which communicates with a space between the inner portion of the pipe-like member 17 and the outer portion of the drive shaft 18.

An attachment portion 26 to the movable handle 12b is formed on the proximal side of the drive shaft 18. The attachment portion 26 is detachably pivoted and connected by a drive shaft fixing member 27 (see FIG. 1) provided to the movable handle 12b. Therefore, the drive shaft 18 moves along its axial direction (moves back and forth) within a predetermined range by a swiveling operation of the movable handle 12b with respect to the fixed handle 12a with the pivot 13 being determined as a supporting point.

As shown in FIGS. 1 and 2, a flexible tube 28 is connected with a rear portion of the drive shaft 18 and extended toward the rear side. An electrical connector 29 is arranged at a rear end of the tube 28. The electrical connector 29 is connected with the power supply apparatus 3 through the connection cord 4. A bend stopper 31a formed of an elastic member is arranged on an outer periphery of a connection portion between the tube 28 and the drive shaft 18. It is preferable for the bend stopper 31a to cover the tube 28 for an appropriate length. A bend stopper 31b formed of an elastic member is likewise arranged on an outer periphery of a connection portion between the tube 28 and the electrical connector 29. Therefore, the tube 28 resists bending and is protected by the two bend stoppers 31a and 31b in order to avoid damage even if it is bent.

As shown in FIG. 4, a treatment portion 9 is arranged at a distal end portion of the insertion section 8 (drive shaft 18). The treatment portion 9 includes a pair of jaws 33a and 33b (one jaw is determined as a first jaw 33a, and the other jaw is determined as a second jaw 33b). The first and second jaws 33a and 33b are connected with each other by a common pivot 35 on a proximal end portion side of these jaws 33a and 33b. Therefore, the first and second jaws 33a and 33b swivel to be opened/closed to each other with the pivot 35 at the center.

As shown in FIGS. 3A and 4, one side of the first jaw 33a which is in close vicinity to the second jaw 33b is formed as a blade portion (heat transfer member) 48 having a substantially cutting tool-like shape. As shown in FIGS. 3A to 3D, a backside of the first jaw 33*a*, i.e., the side apart from the second jaw 33*b* is formed into a smooth curved surface shape without irregularities. Therefore, for example, tissue can be prevented from being caught on the backside of the first jaw 33*a*. On the other hand, as shown in FIG. 4, the second jaw 33*b* is formed as a catch portion which accepts the blade portion 48 of the first jaw 33*a*.

As shown in FIG. 3A, a base 37 which is connected with the drive shaft 18 and the second jaw 33*b* is provided at the proximal end portion of the first jaw 33*a*. The proximal end portion of the base 37 is pivoted at the distal end portion of the drive shaft 18 by a drive pin 38 which is provided in a direction orthogonal to the axial direction (direction to move back and forth) of the drive shaft 18. Therefore, the first jaw 33*a* is swiveled at the distal end portion of the drive shaft 18 with the drive pin 38 being determined as a pivot.

As shown in FIG. 4, a base 40 which is connected with the base 37 of the first jaw 33*a* is provided at the proximal end portion of the second jaw 33*b*. The protrusion 17*a* is provided at the distal end portion of the pipe-like member 17 as described above. The base 40 of the second jaw 33*b* is pivoted on the protrusion 17*a* of the pipe-like member 17 by a pin 41 which is provided in a direction orthogonal to the axial direction at the distal end portion of the pipe-like member 17 and parallel with the drive pin 38. Therefore, the second jaw 33*b* is swiveled with respect to the protrusion 17*a* of the pipe-like member 17 with the pin 41 being determined as a pivot. The pin 41 fixes the base 40 and the proximal end portion of the jaw main body (holding portion main body) 42. Therefore, the pin 41 is a fixing pin which fixes the base 40 of the second jaw 33*b* and the jaw main body 42.

A catch portion 43 with which an edge portion 48*a* of the blade portion 48 of the first jaw 33*a* comes into contact is provided to the jaw main body 42 of the second jaw 33*b*. The catch portion 43 is formed of a soft material having heat-insulating properties or heat resisting properties such as a silicone rubber material or a fluoropolymers material. Therefore, even if the blade portion (heat transfer means) of the first jaw 33*a* is inclined in a front, back, right or left direction to some extent, an entire length of the blade portion 48 is brought into contact with the catch portion 43 by firmly closing both the jaws 33*a* and 33*b*.

A pivot 35 which pivotally supports both bases 37 and 40 of the pair of jaws 33*a* and 33*b* is provided to both bases 37 and 40 in parallel with the drive pin 38 and the pin 41. The pivot 35 is provided on the distal end side of the base 37 of the first jaw 33*a* and at the proximal end portion of the base 40 of the second jaw 33*b*. Therefore, the pair of jaws 33*a* and 33*b* swivel with respect to the mutual jaws 33*a* and 33*b* by the pivot 35, and are opened and closed. The pair of jaws 33*a* and 33*b* are prevented from swiveling in the upward and downward directions beyond predetermined positions.

As shown in FIGS. 3A to 3D, the first jaw 33*a* includes a jaw main body (holding portion main body) 50 as an outer frame on the distal end side of the base 37. The jaw main body 50 is formed of, e.g., a metallic material such as stainless steel or titanium, or a hard plastic material such as LCP.

Figure 3B:
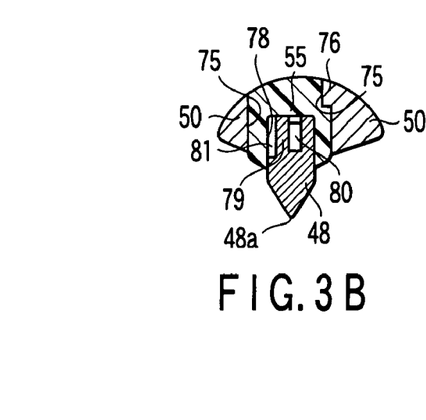
FIG. 3B is a cross-sectional view taken along the line 3B-3B in FIG. 3A according to the first embodiment.

As shown in FIG. 3B, a window portion 75 which vertically pierces the side which is in close proximity to the second jaw 33*b* and the backside of the first jaw 33*a* is formed at a substantially central portion of the jaw main body 50. To the window portion 75 is arranged a heat-insulating member (heat-insulating frame) 55 which has an appropriate height and thickness (wall thickness portion) and the backside having a substantially dome-like cross-sectional shape. As the heat-insulating member 55, for example, a fluoropolymers material, a silicone rubber material, a ceramic material or the like is used. Therefore, the heat-insulating member 55 can insulate the heat generated from a later-described heater 80, and enhance the heat transfer efficiency to the heat transfer member (blade portion) 48.

In order to arrange the heat-insulating member 55 in the window portion 75 of the jaw main body 50, an uneven portion (irregular portion) 76 is formed to each of the heat-insulating member 55 and the jaw main body 50. The jaw main body 50 is combined with the heat-insulating member 55 by their uneven portions 76. At this time, a surface of the heat-insulating member 55 on the backside is smoothly connected with a surface of the jaw main body 50 on the backside without irregularities.

A U-shaped groove (concave portion) 78 having a reverse U shape is provided on the side of the heat-insulating member 55 which is in close proximity to the second jaw 33*b* (lower side in FIG. 3B). A heat transfer member (blade portion) 48 which receives the heat from the later-described heater and applies a heat treatment to tissue is arranged to the U-shaped groove 78. The heat transfer member 48 is formed of a material such as copper, a copper base alloy, an aluminum base alloy, tungsten or molybdenum which efficiently transfers heat. An outer surface of the heat transfer member 48 is covered with a film which is thin and has non-adhesion and heat resisting properties, such as a fluoropolymer, in order to prevent tissue or blood from adhering on the outer surface.

A cross section of the heat transfer member 48 is formed into a substantially rectangular shape in the U-shaped groove 78 of the heat-insulating member 55. It is elongated toward an edge portion 48*a* which is in close proximity to the second jaw 33*b* and formed into a substantially blade-like shape (V shape) or a tapered shape. The edge portion 48*a* is formed in such a manner that the side which is in close proximity to the second jaw 33*b* is formed straight. Therefore, the heat transfer member 48 can suppress a contact area with the outside, prevent the heat from being released, and concentrate the heat on the edge portion 48*a* of the heat transfer member 48.

A space whose cross-section has a substantially rectangular shape (substantially U-shaped concave portion) 79 is formed on the side of the heat transfer member 48 which is in close proximity to the heat-insulating member 55. A heater (heating means) 80 which is arranged in contact with the heat transfer member 48, generates heat when energized and transmits the heat to the heat transfer member 48 is arranged in the space 79. As the heater 80, there is used, e.g., a heat generation element such as a thin film resistance heating element or a thick film resistance heating element or a member such as a nichrome wire which converts an electric power into heat. Further, a ceramic heater, a cartridge heater, a PTC heater or the like can be used as the heater 80. The heater 80 has a cross section formed into a rectangular shape in order to increase a contact area with the heat transfer member 48 as much as possible, and is arranged in the space 79 of the heat transfer member 48.

A small space 81 whose cross section has, e.g., a rectangular shape is provided between the heat transfer member 48 and the heat-insulating member 55. A plurality of leads 70 (70*a*, 70*b*) electrically connected with the heater 80 are arranged in the small space 81, and extend toward the rear side. Each lead 70 is covered with a heat-resistant nonconductive tube. It is to be noted that the plurality of heaters 80 are aligned along the longitudinal direction of the first jaw 33a.

As shown in FIG. 3A, concave catch portions 52 and 53 are provided at the distal and proximal end portions of the jaw main body 50 of the first jaw 33a. The catch portions 52 and 53 of the jaw main body 50 are assembled to engagement convex portions 56 and 57 which are provided to the distal and proximal end portions of the heat-insulating member 55. Pinholes are respectively provided to the distal and proximal end portions of the heat-insulating member 55, pins 58 and 59 are respectively arranged in these pinholes, and the distal and proximal end portions of the blade portion 48 are attached to the heat-insulating member 55 (see FIG. 3C).

Figure 3C:
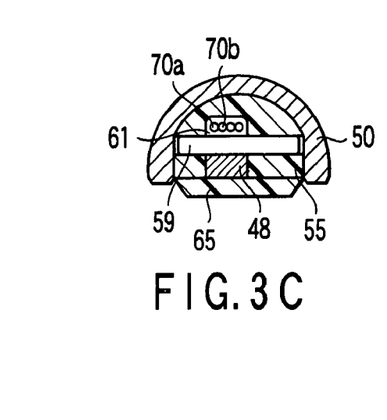
FIG. 3C is a cross-sectional view taken along the line 3C-3C in FIG. 3A according to the first embodiment.
Figure 3D:
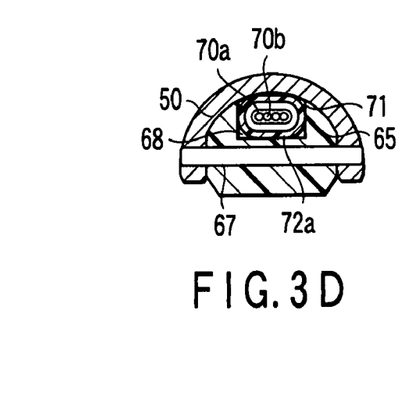
FIG. 3D is a cross-sectional view taken along the line 3D-3D in FIG. 3A according to the first embodiment.

As shown in FIG. 3C, a space 61 is formed between the pin 59 and the heat-insulating member 55. The leads 70 are arranged in the space 61, and extend toward the rear side. As shown in FIGS. 3A to 3D, a fixing member 65 which fixes the blade portion 48, the heat-insulating member 55 and the proximal end portion of the jaw main body 50 is arranged at a lower end of the blade portion 48. As shown in FIG. 3D, the fixing member 65 is fixed to the jaw main body 50 by a pin 67. A space 68 is formed at an upper portion of the pin 67 and at a position which is in contact with the periphery of the jaw main body 50. A tube 71 which covers the plurality of leads 70 is fixed in the space 68 by a fixing bracket 72a. The leads 70a and 70b are bundled into one in the vicinity of the rear end of the blade portion 48. As shown in FIG. 3A, the base 37 of the first jaw 33 is integrally attached to the fixing member 65.

As shown in FIG. 3A, the tube 71 which includes the leads 70 extends to the front side alongside (upper side) of the fixing pin 41, the pivot 35 and the drive pin 38. The other end of the tube 71 is fixed on the inner periphery of the hole portion 19 of the drive shape 18 by a fixing bracket 72b. The leads 70 are led to the connector 29 through the hole portion 19 of the drive shaft 18 and the tube 28 (see FIGS. 1 and 2). Therefore, when the heater 80 is energized by the power supply apparatus 3 through the connection cord 4, the electrical connector 29 and the leads 70, the heater 80 is caused to generate heat.

Figure 5:
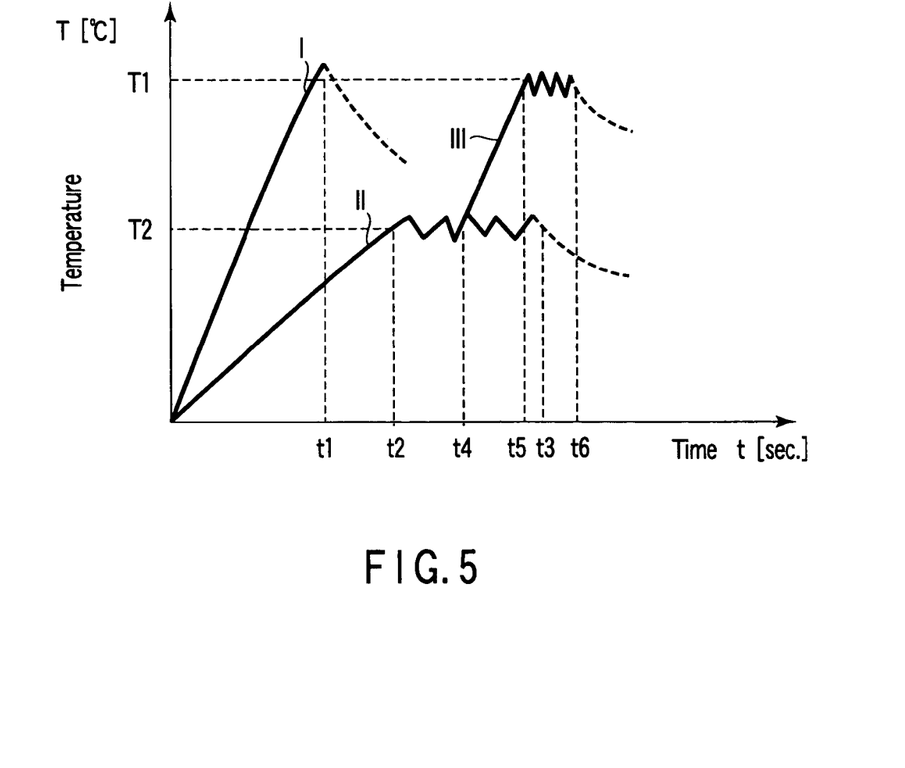
FIG. 5 is a graph showing a temperature of a heater which is controlled by a power supply apparatus in the medical instrument system according to the first embodiment.

FIG. 5 shows temperature change curves of the heater 80 at the time of incision, coagulation and coagulation/incision of tissue, in which a horizontal axis represents a time t (seconds) and a vertical axis represents a temperature T (° C.). It is preferable that the power supply apparatus 3 shown in FIG. 1 includes a control means which can increase a temperature of the heater 80 as indicated by, e.g., curves I, II and III shown in FIG. 5. That is, the power supply apparatus 3 is set in order to rapidly increase a temperature of the heater 80 to $T_1$ in a short time ($t_1$) at the time of incision as indicated by the curve I. The apparatus 3 is set in order to increase the temperature to $T_2$ gradually (in a time $t_2$) and maintain it for several seconds ($t_3$ to $t_2$) at the time of coagulation as indicated by the curve II. The apparatus 3 is set in order to gradually increase the temperature to $T_2$ and then increase the temperature to $T_1$ rapidly (in a time from $t_5$ to $t_4$) at the time of coagulation and incision as indicated by the curve III. This temperature $T_1$ is, e.g., 200° C., and the temperature $T_2$ is, e.g., 180° C.

The operation of the medical instrument system 1 will now be described.

An operator swivels the movable handle 12b around the pivot 13 of the fixed handle 12a and the movable handle 12b of the operation section 7 in the treatment instrument 2 shown in FIG. 1. That is, the movable handle 12b is moved close to or away from the fixed handle 12a in directions indicated by arrows α and β in FIG. 1. The attachment portion 26 on the front side of the drive shaft 18 is moved back and forth in order to move the drive shaft 18 back and forth. With the forward or rearward movement of the drive shaft 18, the drive pin 38 at the distal end of the drive shaft 18 moves back and forth (moves forward and rearward) with respect to the pipe-like member 17.

As shown in FIG. 1, the movable handle 12b is opened in the direction indicated by the arrow α with respect to the fixed handle 12a from a state in which the pair of jaws 33a and 33b are closed. The drive shaft 18 is moved forward with respect to the pipe-like member 17. The base 37 of the first jaw 33a pivotally supported by the drive pin 38 at the distal end of the drive shaft 18 moves forward as indicated by broken lines in FIG. 6 with the forward movement of the drive shaft 18.

Figure 6:
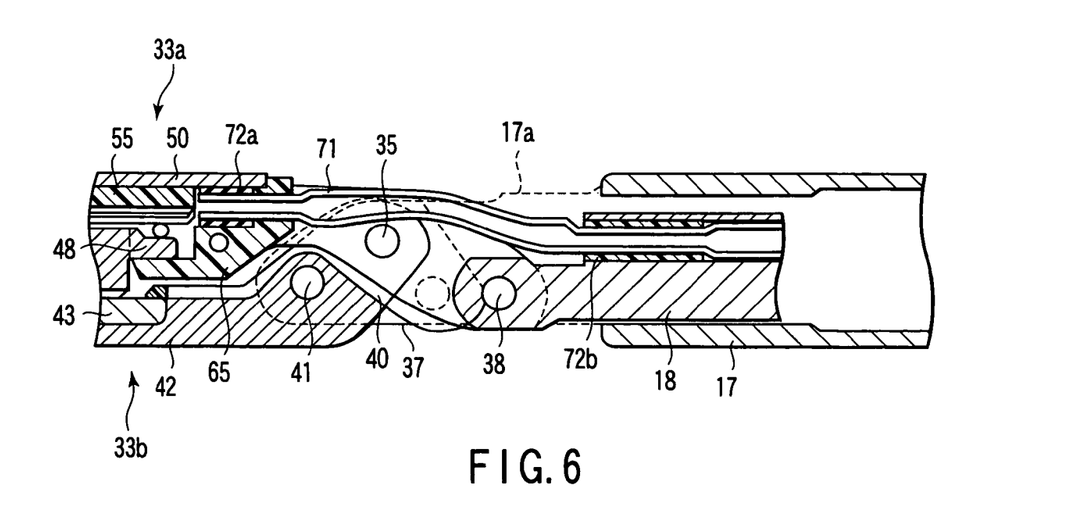
FIG. 6 is a cross-sectional view showing the vicinity of a boundary portion between an insertion section and a treatment portion of the instrument in the medical instrument system according to the first embodiment.

At this time, a position of the fixing pin 41 of the base 40 of the second jaw 33b is not changed with respect to the pipe-like member 17. That is, the pin 41 does not move up and down nor move back and forth with respect to the pipe-like member 17. A distance between the pivot 35 and the fixing pin 41 is not changed.

When the base 37 of the first jaw 33a moves forward, the pivot 35 also moves forward. At this time, the fixing pin 41 swivels there, but its position does not change. When the pivot 35 moves forward, the pivot 35 swivels around the fixing pin 41 and moves toward the upper side of the fixing pin 41. That is, the base 40 of the second jaw 33b swivels with the fixing pin 41 being used as a pivot. At this time, the pivot 35 is moved to the upper front side by swiveling of the fixing pin 41 there. The second jaw 33b swivels toward the lower side.

On the other hand, when the pivot 35 is moved to the upper front side of the fixing pin 41 with the forward movement of the drive pin 38, the base 37 of the first jaw 33a swivels toward the upper and front side with the drive pin 38 being used as a pivot. The first jaw 33a swivels toward the upper side while moving forward. That is, as shown in FIG. 4, the first jaw 33a and the second jaw 33b are opened each other with the pivot 35 being used as a supporting point. When closing the pair of jaws 33a and 33b, the movable handle 12b shown in FIG. 1 is closed in the direction indicated by the arrow β (see FIG. 1) with respect to the fixed handle 12a. The drive shaft 18 is moved back with respect to the pipe-like member 17, thereby providing the opposite behavior.

When the pair of jaws 33a and 33b are opened/closed, the flexible tube 71 provided between the first jaw 33a and the hole portion 19 of the drive shaft 18 bends in accordance with opening/closing of the jaws 33a and 33b. The leads 70 arranged in the flexible tube 71 are protected in the flexible tube 71, thereby preventing an unreasonable force from being applied.

When the rotational operation section 16 provided on the distal end side of the insertion section main body 21 is swiveled around the axis of the insertion section 18 with the operation section 7 being fixed, the pipe-like member 17, the drive shaft 18 and the treatment portion 9 swivel around the axis of the insertion section 8.

When the insertion section fixing member 15 of the operation section main body 11 and the drive shaft fixing member 27 of the movable handle 12b are removed, the insertion section 8 and the treatment portion 9 can be removed from the operation section 7 and replaced.

A description will now be given as to the operation when coagulating/incising a coagulation/incision target part of tissue by using the medical instrument system 1.

The power supply apparatus 3 is set in which a manner that the heater 80 increases a temperature along the curve II shown in FIG. 5.

An operator holds the operation section 7 and swivels the movable handle 12b with respect to the fixed handle 12a in the direction indicated by the arrow α shown in FIG. 1. The drive shaft 18 moves forward and the pair of jaws 33a and 33b are opened. The instrument 2 is moved forward in this state, and the coagulation/incision target part of the tissue is interposed between the jaws 33a and 33b. The movable handle 12b is swiveled in the direction indicated by the arrow β depicted in FIG. 1. The drive shaft 18 moves back and the jaws 33a and 33b swivel in the closing direction.

A pressure is applied on the coagulation/incision target part of the tissue by a relatively small pressurizing force which is suitable for the coagulation treatment, and this part is held. That is, the blade portion (heat transfer member) 48 is in contact with the coagulation/incision target part of the tissue. When the foot switch 5 is operated in this state, an electric signal from the foot switch 5 is inputted to the power supply apparatus 3 through the cord 4a. A predetermined current is caused to flow through the treatment instrument 2 from the power supply apparatus 3 through the cord 4. Therefore, the current set in the power supply apparatus 3 flows through the heater 80 provided to the first jaw 33a from the connector 29 through the leads 70. The energized heater 80 generates heat to a predetermined temperature as indicated by, e.g., the curve II in FIG. 5.

With heat generation of the heater 80, a temperature of the heat transfer member 48 which is in contact with the heater 80 is gradually increased. When a temperature of the heater 80 is maintained for an appropriate time, the temperature of the heat transfer member 48 is also maintained. In this state, the part (tissue) of the tissue with which the heat transfer member 48 is brought into contact is coagulated. At this time, heat is difficult to be transferred to the jaw main body 50 of the first jaw 33a by heat generation of the heater 80 since the heater 80 is covered with the heat-insulating member 55 having an appropriate thickness in the window portion 75. Therefore, the heat is efficiently transferred from the heater 80 to the heat transfer member 48, thereby efficiently cauterizing (coagulating) the tissue.

Subsequently, when the foot switch 5 is operated, the current set in the power supply apparatus 3 is passed to the heater 80. At this moment, as indicated by the curve III in FIG. 5, a temperature of the heater 80 is rapidly increased to $T_1$. The movable handle 12b is further swiveled in the direction indicated by the arrow β, i.e., a direction to close the jaws 33a and 33b. Then, the drive shaft 18 moves back, the jaws 33a and 33b are further closed, and the tissue at a part with which the heat transfer member 48 is brought into contact is incised.

As described above, the medical instrument system 1 of the present embodiment obtains the following effect.

The heat-insulating member 55 is arranged in the window portion 75 of the jaw main body 50 of the first jaw 33a, and a part of the heater 80 is covered with the heat-insulting member 55. Therefore, the heat generated by the heater 80 can be prevented from being released to the jaw main body 50, and the heat generated by the heater 80 can be efficiently (unwastefully) transferred to the tissue.

Since the heat-insulating member 55 has a height and a thickness exposed on the backside of the first jaw 33a, i.e., even a small, thin jaw has a wall thickness portion in the heat-insulating member 55, it has heat-insulating properties sufficient to insulate the heat generated from the heater 80. Therefore, the heat generated by the heater 80 can be prevented from being released to the jaw main body 50 of the first jaw 33a. That is, the heat transfer efficiency from the heater 80 to the heat transfer member 48 can be further improved.

The backside surface of the heat-insulating member 55 is smoothly connected with the backside surface of the jaw main body 50 of the first jaw 33a without irregularities. Therefore, tissue cannot be caught even if an operation to ablate the tissue is performed on the smooth surface on the backside with the jaws 33a and 33b being closed. Even in the case of performing an operative treatment, e.g., handling restiform tissue such as a vein or a nerve at the end of the jaw 33a, this treatment can prevent to be caught.

The irregular portion 76 in which the jaw main body 50 is combined with the heat-insulating member 55 over the substantially entire length is formed to the window portion 75 of the jaw main body 50 of the first jaw 33a. Therefore, even if opening/closing of the jaws 33a and 33b or an operation to ablate tissue by using the jaws 33a and 33b is carried out, existence of the window portion 75 piercing the first jaw 33a can avoid displacement toward the backside of the jaw 33a. Since the jaw main body 50 is in constant contact with the heat-insulating member 55 at the irregular portion 76, deformation of the first jaw 33a can be avoided. It is difficult for the first jaw 33a to be damaged. Therefore, the rigidity of the jaws 33a and 33b required to open/close the jaws 33a and 33b or perform an operation to ablate tissue by using the jaws 33a and 3b can be assured.

Thus, according to the instrument system 1 of the embodiment, the heat generated by the heater 80 can be unwastefully transferred to target tissue. Since the instrument 2 can be used to firmly hold and fix the heater means, a large deformation or damage is not generated even if tissue is strongly held. That is, since the instrument 2 has durability.

Although the heat-insulating member 55 is arranged in the first jaw 33a in this embodiment, the catch portion 43 of the second jaw 33b may be formed as a heat-insulating member. It is preferable for the heat-insulating member of the catch portion 43 of the second jaw 33b in such a case to have a shape which can cover the entire heat transfer member 48 exposed to the outside. Therefore, the heat generated by the heater 80 can be further efficiently transferred to tissue.

Although the jaw main body 50 of the first jaw 33a is formed of a metallic material or a plastic material in this embodiment, it is preferable to integrally mold the jaw main body 50 by using, e.g., a heat-insulating member. By doing so, the window portion does not have to be formed to the jaw main body 50, thereby facilitating molding and reducing the number of components. Therefore, the first jaw 33a itself can be reduced in size (size can be prevented from being increased). Further, the heat-insulating properties can be enhanced, and the heat transfer efficiency to the heat transfer member 48 can be increased.

The pipe-like member 17 and the drive shaft 18 constituting the insertion section 8 are formed as hard members in this embodiment. Further, it is possible to obtain a soft treatment instrument with the good operability in which the insertion section 8 can be curved or bent by forming the pipe-like member 17 and the drive shaft 18 as soft members.

A modification of the pipe-like member 17 and the drive shaft 18 described in conjunction with the first embodiment will now be explained with reference to FIGS. 7A to 7C.

Figure 7A:
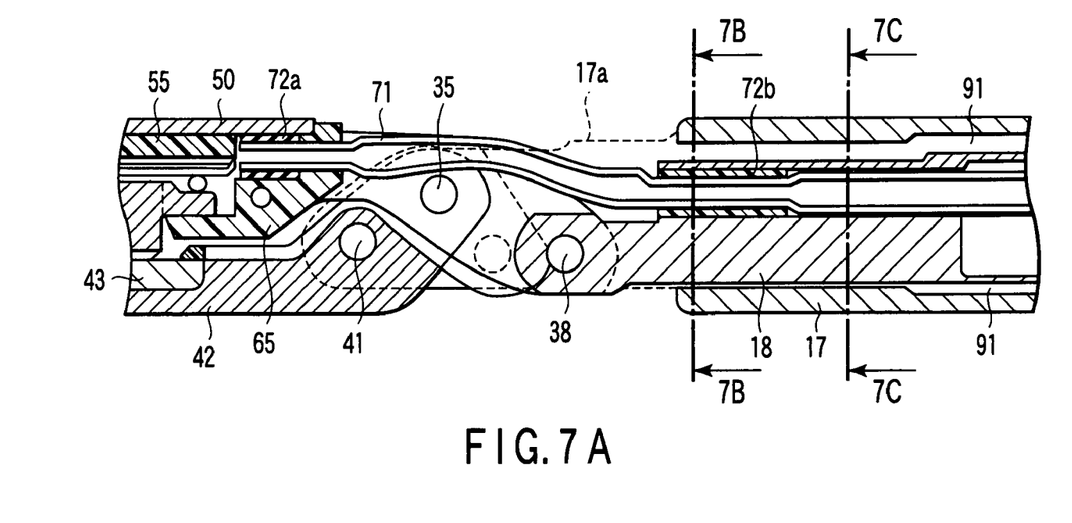
FIG. 7A is a cross-sectional view showing the vicinity of the boundary portion between the insertion section and the treatment portion of the instrument in a modification according to the first embodiment.
Figure 7B:
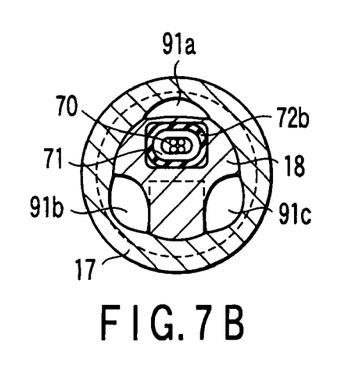
FIG. 7B is a cross-sectional view taken along the line 7B-7B in FIG. 7A according to the first embodiment.
Figure 7C:
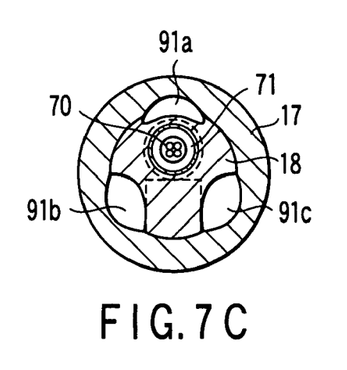
FIG. 7C is a cross-sectional view taken along the line 7C-7C in FIG. 7A according to the first embodiment.

As shown in FIGS. 7A to 7C, spaces (gaps) 91a to 91c (which will be mainly denoted by reference numeral 91 hereinafter) are provided between the pipe-like member 17 and the drive shaft 18. The spaces 91 are caused to communicate with the port 24 (see FIGS. 1 and 2) provided to the insertion section main body 21.

After using the medical instrument system 1, when a cleaning fluid is strongly caused to flow from the port 24 of the instrument 2, the cleaning fluid flows toward the distal end direction of the pipe-like member 17 while cleansing the spaces 91 between the pipe-like member 17 and the drive shaft 18. The rear end side of the pipe-like member 17 is sealed with the seal member 22 shown in FIGS. 1 and 2. Therefore, the cleaning fluid flows toward the outside from the gaps 91 shown in FIGS. 7B and 7C together with contaminations. Thereafter, the gaps 91 are dried by, e.g., supplying air into the gaps 91 from the port 24.

Therefore, it is possible to finely cleanse the spaces 91 between the pipe-like member 17 and the drive shaft 18.

A second embodiment will now be described with reference to FIGS. 8A to 10. A medical instrument (thermocoagulation and cutting forceps) 100 according to the embodiment is a modification of the treatment instrument 2 described in conjunction with the first embodiment.

Figures 8A, 8B, 8C:
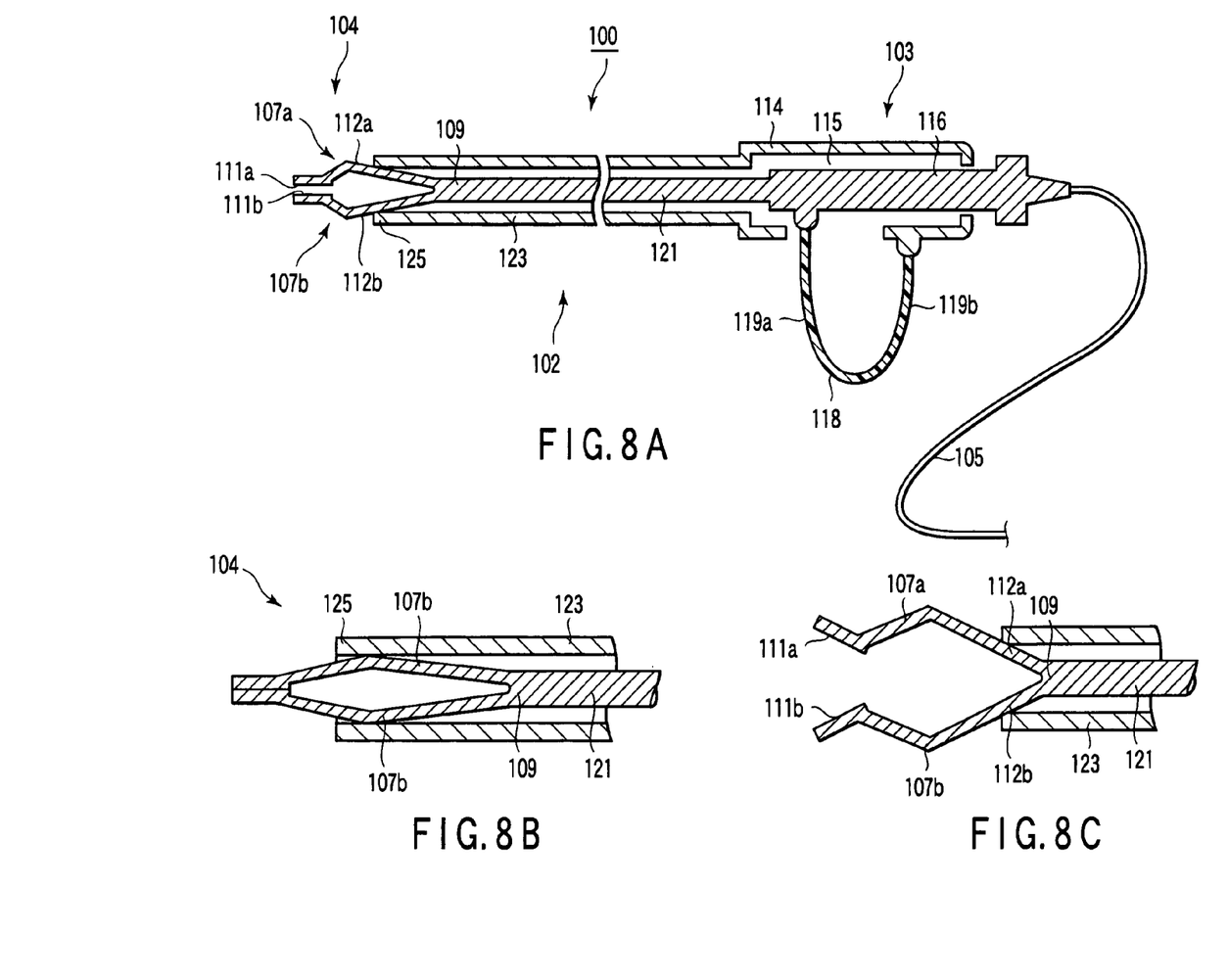
FIG. 8A is a schematic cross-sectional view of an instrument according to a second embodiment.
FIG. 8B is a schematic cross-sectional view showing a state in which a treatment portion of the instrument in FIG. 8A is closed according to the second embodiment.
FIG. 8C is a schematic cross-sectional view showing a state in which the treatment portion of the instrument in FIG. 8A is opened according to the second embodiment.

As shown in FIG. 8A, the medical instrument 100 includes an elongated insertion section 102 and an operation section 103 provided on a proximal end side of the insertion section 102. A treatment portion 104 is provided on a distal end side of the insertion section 102. A long connection cord 105 extends from a rear end of the operation section 103 to the front side, and is connected with a non-illustrated power supply.

A pair of arms 107a and 107b is provided to the treatment portion 104, and proximal end sides of the arms 107a and 107b are integrated by a connection portion 109 of the distal end of the insertion section. Opposed surfaces 111a and 111b which move closer to (see FIG. 8B) or away from each other with a gap therebetween (see FIG. 8C) are formed in the vicinity of and on inner sides of respective distal ends of the arms 107a and 107b. Intermediate or proximal sides of the both arms 107a and 107b are formed of elastic members 112a and 112b having the spring properties.

On the other hand, the operation section 103 includes a substantially cylindrical housing 114 having a through hole on a lower side thereof. A driver (drive shaft) 116 is provided in a space 115 in the housing 114. The driver 116 can move in forward and rearward directions (move back and forth) in the space 115 in the housing 114 without restraint. A part of the housing 114 is connected with a part of the driver 116 by a substantially U-shaped spring 118. One end (distal end) of the spring 118 is connected with the driver 116, and the other end (proximal end) of the same is connected with the housing 114. The spring 118 presses the driver 116 against the housing 114 in a direction toward the distal end. Front and rear portions of the spring 118 are formed as finger holding portions 119a and 119b in which a finger of an operator is caught and held. Therefore, when the finger holding portions 119a and 119b are strongly grasped and the spring 118 is compressed, the driver 116 moves to the proximal side.

The driver 116 and the connection portion 109 are connected with each other by a drive wire (drive shaft) 121. The drive wire 121 transmits motions (forward and rearward operations) of the driver 116 to the connection portion 109. The outer periphery of the drive wire 121 is covered with a tubular member 123 connected with the housing 114 of the operation section 103 in such a manner that the drive wire 121 can move forward or rearward. A distal end of the tubular member 123 is formed as a guide portion (deflection means) 125 of the arms 107a and 107b. Therefore, the arms 107a and 107b come into contact with the guide portion 125 with the forward or rearward movements of the drive wire 121, and advance or retire (move) in the front-and-back direction while being opened or closed.

Figure 9A:
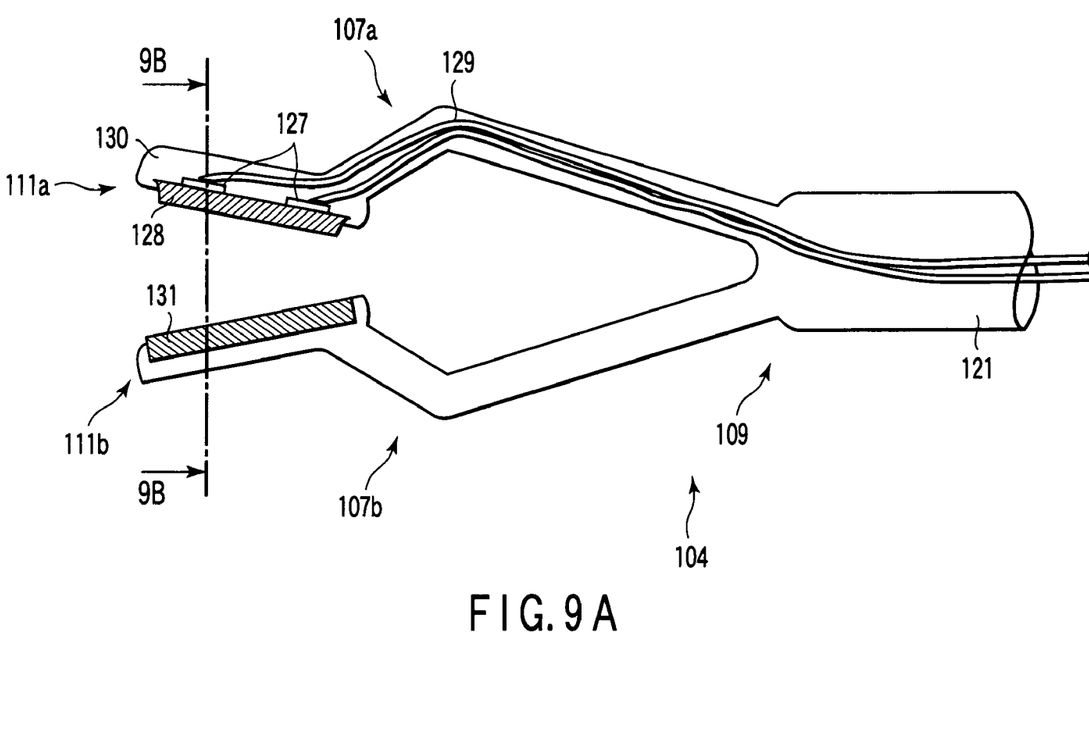
FIG. 9A is a schematic side view showing a state in which the treatment portion of the instrument is opened according to the second embodiment.

FIG. 9A is an enlarged schematic cross-sectional view of the treatment portion 104. One or more (two in this example) heaters (heating means) 127 which generate heat when energized are provided on the opposed surface 111a of one arm 107a. As the heater 127, there is used a member which converts an electrical power into the heat, for example, a heating element such as a thin film resistance heating element or a thick film resistance heating element or a nichrome wire. Further, a ceramic heater, a cartridge heater, a PCT heater or the like is used as the heater 127. A heat transfer surface 128 which is exposed toward the opposed surface 111b of the other arm 107b is provided on the opposed surface 111a on which the heaters 127 are disposed is provided in such a manner that it is in contact with the heaters 127. The heat transfer surface 128 is formed of a metallic material such as copper, a copper base alloy, an aluminum base alloy, tungsten or molybdenum which efficiently transmits heat.

Figure 9B:
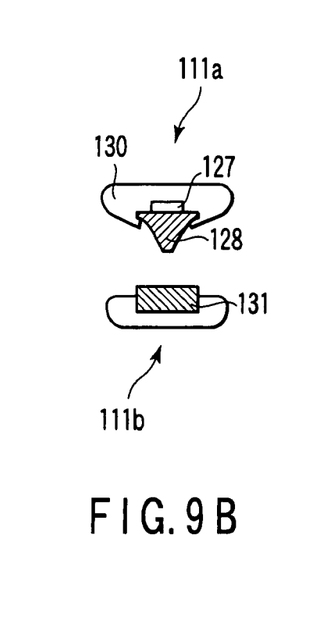
FIG. 9B is a cross-sectional view taken along the line 9B-9B in FIG. 9A according to a second embodiment.

As shown in FIG. 9B, the heat transfer surface 128 of the opposed surface 111a is formed into a tapered shape which becomes thinner as it gets closer to the opposed surface 111b side of the other arm 107b. It is formed into such a shape in order to reduce a contact area with the outside, increase the heat transfer efficiency, concentrate the heat on a part and improve the incision properties. The outer surface of the heat transfer surface 128 is covered with a thin film with the non-adhesiveness such as a fluoropolymer in order to prevent tissue or blood from adhering.

As shown in FIG. 9A, in the heater 127, a plurality of leads 129 extend to the driver 116 on the proximal side through the inside of the arm 107a, the connection portion 109 and the drive wire 121. Incidentally, it is preferable that an insulating coating is applied on the lead 129, and the arm 107a, the connection portion 109 and the drive wire 121 are also formed of heat resisting non-conductors such as a resin in order to avoid the electrical influence of the leads 129 or the influence of heat. An end portion of each lead 129 is connected with a non-illustrated power supply by the connection cord 105. Therefore, the heaters 127 are energized from the power supply through the connection cord 105 and the leads 129 and generate heat. The heaters 127 and the heat transfer surface 128 are covered with a heat-insulating material 130. As the heat-insulating material 130, a fluoroplastics or PEEK (polyether ether ketone) can be considered. Therefore, when the heaters 127 generate heat, the heat is difficult to be released from the heat-insulating material 130, thereby efficiently transferring the heat to the heat transfer surface 128. Incidentally, as described with reference to FIG. 6 in the first embodiment, it is preferable for the power supply to be able to control a temperature of each heater 127.

A catch surface 131 which comes into contact with the heat transfer surface 128 having the heaters 127 attached thereto when closed is provided on the opposed surface 111b of the arm 107b on the opposed side. The catch surface 131 is formed of a material having the heat resisting properties and the heat-insulating properties. As a material of the catch surface 131, a silicone rubber material or a fluoroplastics material is used, for example. The heaters 127, the heat transfer surface 128 and the leads 129 equal to those of the arm 107a may be incorporated in the arm 107b in place of the catch surface 131.

An operation of the medical instrument 100 will now be described.

The finger hold portions 119a and 119b shown in FIG. 8A are strongly held, the spring 118 is compressed and held, the driver 116 is pulled toward the proximal side, and the drive wire 121 is pulled toward the proximal side. The connection portion 109 is pulled into the inner side of the guide portion 125. With this operation, the arms 107a and 107b are pressed by the guide portion 125 and biased to the inner side of the tubular member 123, and the opposed surfaces 111a and 111b come into contact with each other (see FIG. 8B). That is, the opposed surfaces 111a and 111b are closed.

The finger hold portions 119a and 119b shown in FIG. 8A are released. The driver 116 is pressed toward the distal end side, and the drive wire 121 is thrusted toward the distal end on the front side. Then, the connection portion 109 moves forward to the vicinity of the guide portion 125. With this operation, the arms 107a and 107b move to the outer side by their own elasticity without being closed inside the tubular member 123 by the guide portion 125, and the opposed surfaces 111a and 111b are opened with a gap therebetween (see FIG. 8C).

The treatment portion 104 is thrusted into the guide portion 125 of the tubular member 123, and the arms 107a and 107b are opened/closed. That is, the arms 107a and 107b are opened/closed and deflected while being thrusted into the guide portion (deflection means) 125 by holding and releasing the spring 118 provided to the operation section 103. After bringing tissue into contact with the arms 107a and 107b being opened, the arms 107a and 107b are closed, and the tissue is held between the arms 107a and 107b with an appropriate force. The heaters 127 are energized from the power supply through the connection cord 105 and the leads 129, the heaters 127 are caused to generate heat to a predetermined temperature, and the heat is transferred to the heat transfer surface 128. Therefore, the tissue is thermally coagulated on the heat transfer surface 128. When the temperature of the heaters 127 is further increased, the tissue is incised.

The description has been given as to the example in which the number of arms 107a and 107b of the treatment portion 104 is two in this embodiment. Further, the advantages remain the same even if the number of arms is one or three or more (multiple number). For example, when three arms are provided at equal intervals, the arms are formed into a bud-like shape and opened/closed.

As described above, according to the embodiment, even though the structure is simple, the stable coagulation capability and the incision capability can be demonstrated, and it is possible to form the medical instrument 100 in which the insertion section 102 or the treatment portion 104 are further reduced in thickness and size. The heaters 127 and the heat transfer surface 128 are covered with the heat-insulating material 130. Therefore, even if the heaters 127 generate heat, a change in temperature of the heat-insulating material 130 is small, and tissue can be prevented from adhering to the treatment portion 104 (heat-insulating material 130). Therefore, a reduction in treatment efficiency can be avoided, and problems related to cleaning can be reduced.

Since a high-frequency current or the like is not used, the power supply can be simplified and reduced in size. Further, by setting the heaters 127 to control a temperature, i.e., allow a desired current to flow from the power supply, a thermal coagulation degree according to an application can be obtained.

Figure 10:
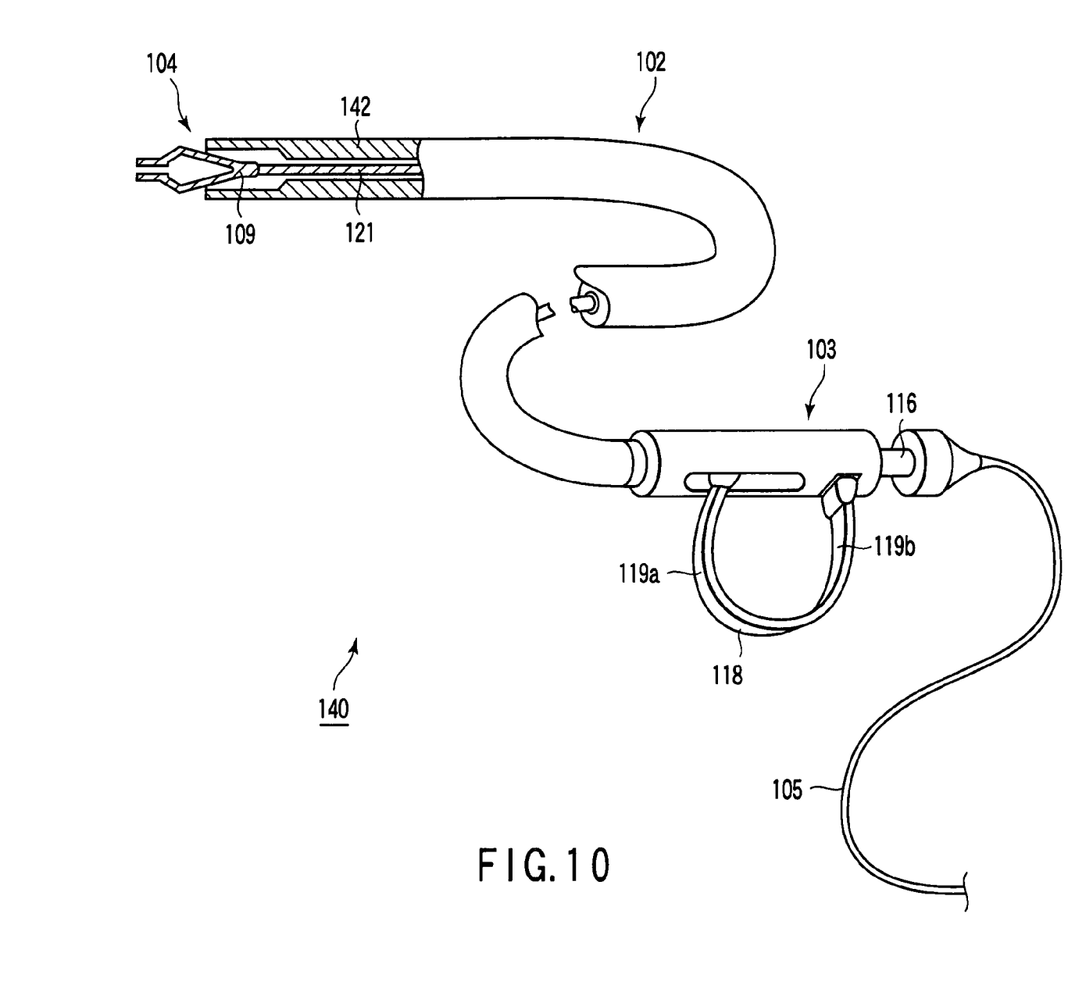
FIG. 10 is a schematic partial cross-sectional perspective view in a modification according to the second embodiment.

It is to be noted that, as shown in FIG. 10, the tubular member 142 of the medical instrument 140 is formed in such a manner that its inner periphery has a different wall thickness, from the vicinity of the distal end portion to the proximal end portion, from the tubular member 123 of the treatment instrument 100 depicted in FIG. 8A. Therefore, when the finger holding portions 119a and 119b of the spring 118 are strongly held and the treatment portion 104 is pulled toward the inside, the connection portion 109 of the treatment portion 104 is brought into contact with the distal end portion of the wall thickness portion of the tubular member 142 of the treatment portion 104. Then, an operator does not feel the pressure due to contact and an additional force does not have to be applied. It is preferable that the distal end portion of the treatment portion 104 is pulled toward the proximal end portion side away from the distal end portion of the tubular member 142 at such a contact position.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A medical instrument comprising:
   an elongated insertion section having distal and proximal end portions;
   a pair of holding portions provided at the distal end portion of the insertion section operative to hold tissue;
   a heat source portion provided on at least one holding portion of the pair of holding portions, the heat source portion operative to generate heat to transfer the heat toward the other holding portion of the pair of holding portions, at least a part of the heat source portion being covered with a heat insulating member disposed along a lengthwise direction of the heat source portion; and
   an operation section provided at the proximal end portion of the insertion section, operative to open and close the pair of holding portions;
   the pair of holding portions comprising:
   a pair of jaws which are able to be opened/closed with respect to each other;
   at least one of the jaws has a jaw main body and a window portion which is provided to the jaw main body and pierced from an opposed surface with respect to the other jaw to the surface of the outer periphery of the jaw main body;
   the heat insulating member is arranged in the window portion in such a state that it is smoothly provided on the surface of the outer periphery; and
   the heat source portion is in contact with a heat transfer portion which transfers the heat generated by the heat source portion toward the other jaw.

2. A medical instrument according to claim 1, wherein the jaw main body is formed of a insulating member.

3. A medical instrument according to claim 2, wherein the insulating member and the jaw main body respectively include irregular portions which are fitted with each other.

4. A medical instrument according to claim 1, wherein the jaw main body and the insulating member are integrally formed.

5. A medical instrument according to claim 1, wherein the insulating member has a wall thickness portion in at least one of an edge portion and the vicinity of the window portion on the outer periphery surface side of the jaw main body.

6. A medical instrument according to claim 1, wherein the heat transfer portion includes a blade portion used to give a medical treatment to a living body.

7. A medical instrument according to claim 1, wherein the insulating member includes an insulating member side concave portion at which the heat source portion and the heat transfer portion are arranged, and the heat transfer portion integrally includes a heat source portion side concave portion at which the heat source portion is arranged and a blade portion which is provided to one jaw main body and received by the other jaw.

8. A medical instrument according to claim 7, wherein the insulating member side concave portion has a substantially U-shaped transverse cross section.

9. A medical instrument comprising:

an elongated insertion section having distal and proximal end portions;

a pair of jaws which are provided at the distal end portion of the insertion section and are able to be opened/closed to each other, at least one of the jaws including:

a jaw main body;

a window portion which is provided to the jaw main body and pierced from an opposed surface facing the other jaw to an outer periphery surface of the jaw main body;

an insulating member which is arranged inside the window portion and smoothly provided on the outer periphery surface;

a heating means which is partially covered with the insulating member and generates heat when energized; and a heat transfer means which is provided in a state that it is in contact with the heating means, and transfers the heat generated by the heating means toward the other jaw; and an operation section which is provided at the proximal end portion of the insertion section and operates the jaws to be opened/closed by an operation of an operator.

10. A medical instrument according to claim 9, wherein the jaw main body is formed of an insulating member.

11. A medical instrument according to claim 10, wherein the insulating member and the jaw main body respectively include irregular portions which are fitted with each other.

12. A medical instrument according to claim 9, wherein the jaw main body and the insulating member are integrally formed.

13. A medical instrument according to claim 9, wherein the insulating member has a wall thickness portion in at least one of an edge portion of the window portion and the vicinity of the same on the outer periphery surface side of the jaw main body.

14. A medical instrument according to claim 9, wherein the heat transfer means includes a blade portion which is used to give a medical treatment to tissue.

15. A medical instrument according to claim 9, wherein the insulating member includes an insulating member side concave portion in which the heating means and the heat transfer means are arranged, and the heat transfer means integrally includes a heat transfer means side concave portion in which the heating means is arranged, and a blade portion which is provided to one jaw main body and received by the other jaw.

16. A medical instrument according to claim 15, wherein the insulating member side concave portion has a substantially U-shaped transverse cross section.

17. A medical instrument system comprising:

an elongated insertion section having distal and proximal end portions;

a first jaw provided at the distal end portion of the insertion section having:

a first jaw main body;

a heat insulating member provided at the first jaw main body;

a heater which arranged such that a significant length of the heater means is covered by the heat insulating member, and comprising a lead wire extending toward the proximal end portion of the insertion section; and a heat transfer means heated by transfer of heat generated by the heater means;

a second jaw provided at the distal end portion of the insertion section having:

a second jaw main body; and a catch portion provided to the second jaw main body and adapted to receive heat from the heat transfer means of the first jaw, a pivot which pivotally supports the first and second jaw main bodies at the distal end portion of the insertion section in such a manner that the first and second jaw main bodies are able to be opened/closed;

an opening/closing mechanism arranged in the insertion section, and operative to open and close the first and second jaw main bodies with respect to each other;

an operation section provided at the proximal end portion of the insertion section, and configured to operate the opening/closing mechanism; and a power supply electrically connected with the lead wire of the heater means and operative to supply power to the heater means;

wherein the first jaw main body includes a window portion which pierces from an outer periphery surface of the jaw main body to an opposed surface facing the second jaw main body, and at least the heat insulating member is arranged at the window portion.

18. A medical instrument system according to claim 17, wherein an engaging irregular portion is arranged on a boundary between the first jaw main body and the heat insulating member.

* * * * *